(12) United States Patent
Roman et al.

(10) Patent No.: US 9,440,113 B2
(45) Date of Patent: Sep. 13, 2016

(54) CARDIO-BASED EXERCISE SYSTEMS WITH VISUAL FEEDBACK ON EXERCISE PROGRAMS

(71) Applicants: Joshua J. Roman, Scituate, MA (US); Michael G. Lannon, Orleans, MA (US); David M. Alexander, Norwell, MA (US); Jeffrey W. Moore, West Barnstable, MA (US); Eric J. Marthinsen, Millis, MA (US)

(72) Inventors: Joshua J. Roman, Scituate, MA (US); Michael G. Lannon, Orleans, MA (US); David M. Alexander, Norwell, MA (US); Jeffrey W. Moore, West Barnstable, MA (US); Eric J. Marthinsen, Millis, MA (US)

(73) Assignee: Michael G. Lannon, Rockland, MA (US)

( * ) Notice: Subject to any disclaimer, the term of this patent is extended or adjusted under 35 U.S.C. 154(b) by 0 days.

(21) Appl. No.: 14/503,655

(22) Filed: Oct. 1, 2014

(65) Prior Publication Data

US 2016/0096069 A1 Apr. 7, 2016

(51) Int. Cl.
*A63B 24/00* (2006.01)

(52) U.S. Cl.
CPC ....... *A63B 24/0062* (2013.01); *A63B 24/0087* (2013.01)

(58) Field of Classification Search
CPC .............. A63B 24/00; A63B 24/0062; A63B 24/0084; A63B 22/0023; A63B 22/02; A63B 24/0087
See application file for complete search history.

(56) References Cited

U.S. PATENT DOCUMENTS

| | | | | |
|---|---|---|---|---|
| 5,240,417 A | * | 8/1993 | Smithson | A63B 21/00181 348/121 |
| 5,782,639 A | * | 7/1998 | Beal | A63B 71/0622 434/29 |
| 5,785,630 A | * | 7/1998 | Bobick | A63B 22/02 482/1 |
| 7,220,219 B2 | * | 5/2007 | Papadopoulos | A63B 22/02 482/54 |
| 8,105,207 B1 | | 1/2012 | Lannon et al. | |
| 8,167,776 B2 | | 5/2012 | Lannon et al. | |
| 2002/0045517 A1 | * | 4/2002 | Oglesby | A63B 22/0023 482/51 |
| 2003/0171190 A1 | * | 9/2003 | Rice | A63F 13/06 482/57 |
| 2005/0075213 A1 | * | 4/2005 | Arick | A63B 24/00 482/1 |
| 2006/0189440 A1 | * | 8/2006 | Gravagne | A63B 24/00 482/8 |
| 2007/0123390 A1 | * | 5/2007 | Mathis | A63B 24/0084 482/8 |

OTHER PUBLICATIONS

"Exercise System with Headphone Detection Circuitry", Inventor Jeffrey Moore, filed Oct. 1, 2014.

* cited by examiner

*Primary Examiner* — Glenn Richman
(74) *Attorney, Agent, or Firm* — Fish & Richardson P.C.

(57) ABSTRACT

In general, a computing device disposed in a cardio exercise machine receives data related to a fitness level of a user. The computing device selects a workout program based at least in part on the data. The operations of the cardio exercise machine are controlled based at least in part on the workout program. The computing device generates visual feedback based on at least one of the user's operation of the cardio exercise machine and the selected workout program measured against performance criteria.

20 Claims, 6 Drawing Sheets

CARDIO-BASED EXERCISE SYSTEMS WITH VISUAL FEEDBACK ON EXERCISE PROGRAMS

BACKGROUND

This invention relates to exercise and more particularly cardio exercise equipment.

Regular exercise and physical activity are both important and beneficial for long-term health and well-being. Some of the benefits of exercise and physical activity include a reduced risk of premature death, heart disease, high blood pressure, cholesterol and a reduced risk of developing colon cancer and diabetes. In addition, the benefits of exercise and physical activity further includes a reduced body weight, a reduced risk of depression and improve psychological well-being.

As such, various types of exercising equipment are currently known that enable an operator to exercise. Some exercising equipment may require the expertise of an instructor or a personal trainer to teach the operator the proper techniques and usage of the equipment. One example of strength training exercise equipment is disclosed in U.S. Pat. No. 8,105,207, assigned to the assignee of the present invention.

SUMMARY

According to an aspect a method includes receiving, by a computing device disposed in a cardio exercise machine, data related to a fitness level of a user, selecting, by the computing device, a workout program based at least in part on the data, controlling operations of the cardio exercise machine based at least in part on the workout program, generating, by the computing device, video feedback based on the user's operation of the cardio exercise machine and the selected workout program, and rendering the video feedback performance on a display with the rendered video feedback performance including a plurality of visual performance data items that include speed and resistance level performance characteristics, with each visual performance data item rendered as a dynamic visualization with respect to the predetermined standard for each performance characteristic in real time.

Aspects also include apparatus and computer program products.

One or more of the following advantages may be provided by one or more aspects of the invention.

A system can determine visual performance data items during exercise and when a user performance indicator is outside calculated performance standard range(s), the system can convey audio instructions to the user to adjust the user's performance to match the calculated performance standard or when it is critically out of scope, render a notice instructing the user to terminate exercising the current exercising instruction, allowing and encouraging a person to exercise as his/her fitness level without plateauing and without overly stressing the individual.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
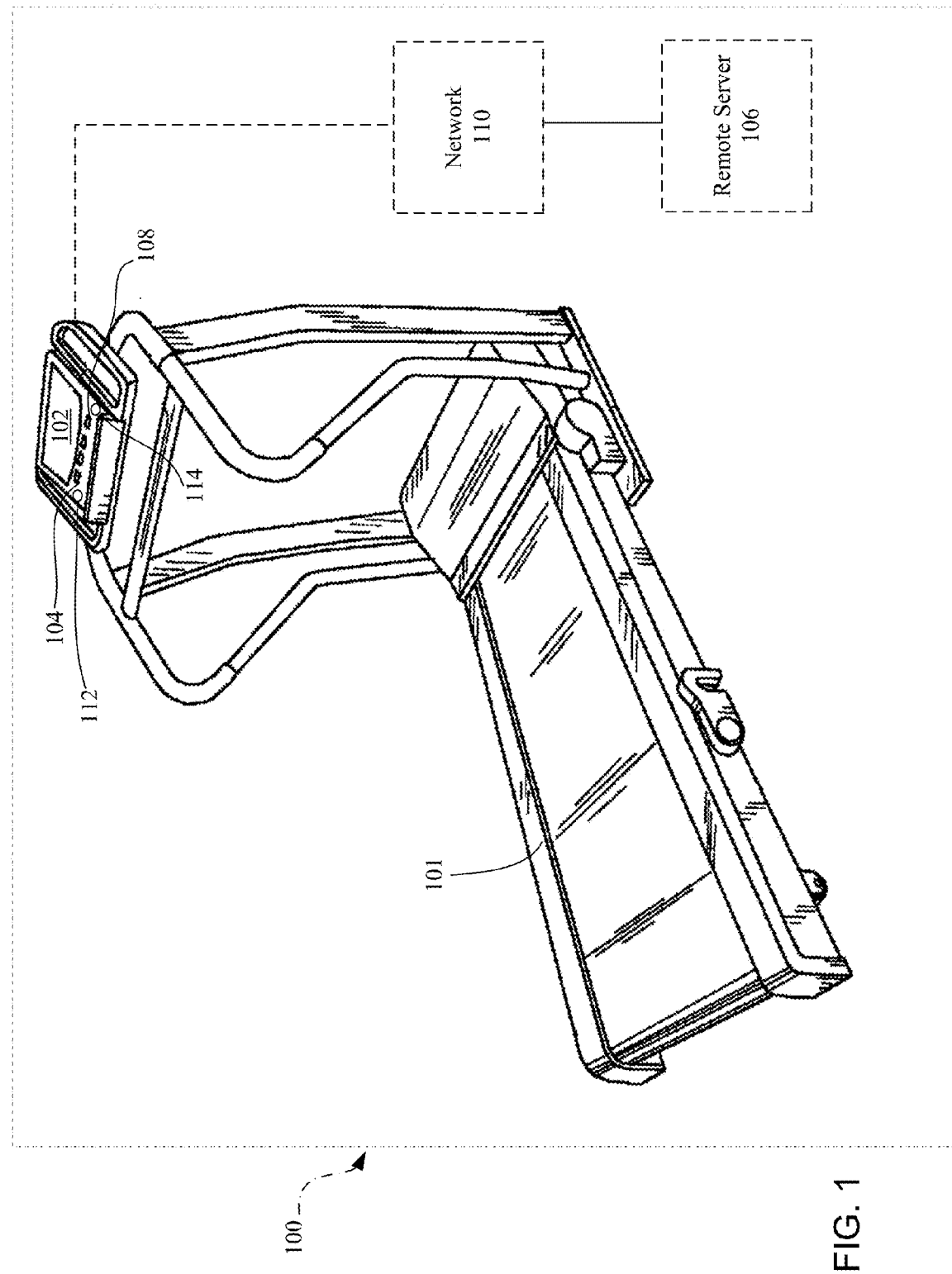
FIG. 1 is a diagram depicting an exercise apparatus.

Referring to FIG. 1, a system 100 is shown to include an exemplary cardio exercise machine 101. While the cardio exercise machine 101 depicted in FIG. 1 is a treadmill, the techniques described below could be implemented in many different types of cardio exercise machines such as stationary bicycles, recumbent stationary bicycles, stair-climbers, elliptical trainers, ski-trainers, rowing machines, step mills, versa climbers, arc trainers, or hand ergometers. A cardio-machine is typically characterized by an exercise that involves significant cardiovascular exertion in contrast to strength machines that are typically involved with weight training Cardio exercise machine 101 enables a user (not shown) to exercise by operating the cardio exercise machine (e.g., by running on the treadmill).

The cardio exercise machine includes an exercise system (FIG. 2) to manage operations of the cardio exercise machine. The exercise system controls the operations of the cardio exercise machine according to data associated with the user (sometimes referred to as "user-specific data") that is stored in a memory device. Examples of a suitable memory device include a removable universal storage bus (USB) storage device, a hard drive on a computer communicating with the exercise machine over a network (e.g., the Internet), or other types of removable storage media, such as compact disks (CDs), digital video disks (DVDs), cassette disks, or floppy disks. In some examples of the memory, a remote server 106 stores the user-specific data in a remote type of storage device, and communicates with the cardio exercise machine over a network 110.

In FIG. 1, the cardio exercise machine is configured to communicate with the memory device via a port 104 into which the memory device may be inserted. In FIG. 1, the memory device is a (USB) storage device. The memory devices may also communicate wirelessly with the cardio exercise machine.

The cardio exercise machine provides a user with a plurality of multi-session cardio programs that are customized to the user's level of fitness. The workouts provided to a user are based on the user-specific data. The user-specific data includes both "personal data" and "performance data." Personal data includes a user's level of fitness that is calculated by the exercise system using a variety of factors such as age, weight, height, gender, and factors determined by a questionnaire where answers are entered into the machine via a graphical user interface rendered by the exercise system on the display 102. Alternatively, the personal data can be obtained by an on-machine testing protocol, such as a stress test that is administered by the machine automatically based on default settings at an initial use, and, which can be administered periodically, thereafter.

For example, the cardio exercise machine 101 includes display 102 that displays questions (e.g., "What is your age?"). The system presents these questions to the user and the user enters answers to these questions in the GUI. The exercise system calculates the user's level of fitness based on the answers to these questions. The user enters responses to the questions by actuating buttons 108 on the cardio exercise machine or by speaking answers to the questions into a microphone (not shown). Other techniques can be used. The user may have the option of changing the personal data if, for example, some of the information contained within the personal data has changed (e.g., if the user has lost weight, the user can update his stored weight).

The exercise system customizes workout programs based on user-data stored from previous workout sessions. This data includes information relating to a user's performance on past workouts, and is sometimes referred to as "performance data." These factors are combined to calculate a "fitness level" (e.g., on a numeric scale of 1-100), where the fitness level is used to modify the intensity and type of various standard workouts. For example, if a user has previously completed a workout program on a treadmill, the user might be assigned a score of "85" by the exercise system based on his performance (e.g., the user might have earned a score of "100" if he had not slowed down during a portion of the workout). A user's fitness level can be modified based on the user's performance during past workout sessions, or by re-entering other personal information.

During a session, the cardio exercise machine provides feedback in the form of exercise guidance and instruction via a combination of on-machine messaging, automatic machine control of speed, incline, intensity, and resistance via the Communications Specification for Fitness Equipment protocol (CSAFE) or other proprietary protocols, and audio-based coaching and content. If a user is exercising on a treadmill, for example, the treadmill could increase the incline and speed of its conveyer belt to augment the intensity of the user's workout. This could be in response to, for example, a scripted workout program, or in response to a user's current workout performance (e.g., by sensing a heart rate of the user).

In some examples, guidance information, such as audio coaching, is received by a user in a number of ways. First, a user may connect an existing personal audio device (e.g. an iPod®, an MP3 player, a CD player, etc.) into a line-in jack 112 on a processor board (FIG. 2), connect user-wearable headphones 208 (FIG. 2) into a line out jack 114 on the processor board. The guidance information may reside wholly or in part on the cardio platform or processor board itself. In some examples, connections between the personal audio device and the processor board can be wireless connections (e.g., a Bluetooth® connection). Once connected, the software automatically fades the user-provided audio (e.g., music) while playing the audio coaching information. The user-provided audio resumes playing, normally, during time intervals where coaching information is not being transmitted. The user can also connect headphones into a line-out jack on the processor board, and the software plays the audio coaching information. In some examples, the user can connect headphones to the personal audio device, and a different connection can link the personal audio device with the processor board. The processor board can also provide music or other content when coaching information is not being transmitted.

Once a session is completed, data pertaining to the user's performance on that session is written to the memory device, and that information is sent to a remote server system where the information is recorded (e.g., remote server 106) such that the information can be viewed via access to a web site. Future exercise sessions and programs are tailored to incorporate a user's past performance(s) and adherence to the past programs and sessions. In some examples, the audio coaching information is generated based upon a user's fitness level and performance data. For example, the audio coaching data could be constructed from a library containing a plurality of workout programs that have associated audio coaching data. A program then selects a workout program based on the personal and performance data specific to the user. In some examples, a customized workout program is constructed for a user by selecting one or more segments from different workout programs and combining them into one customized workout program. Each segment has associated audio coaching data that is combined to present the user with a guided workout program. The custom workout program is stored on one or more of the memory device 212 (FIG. 2) and the remote server 106 for later retrieval and execution by the cardio exercise machine.

Figure 2:
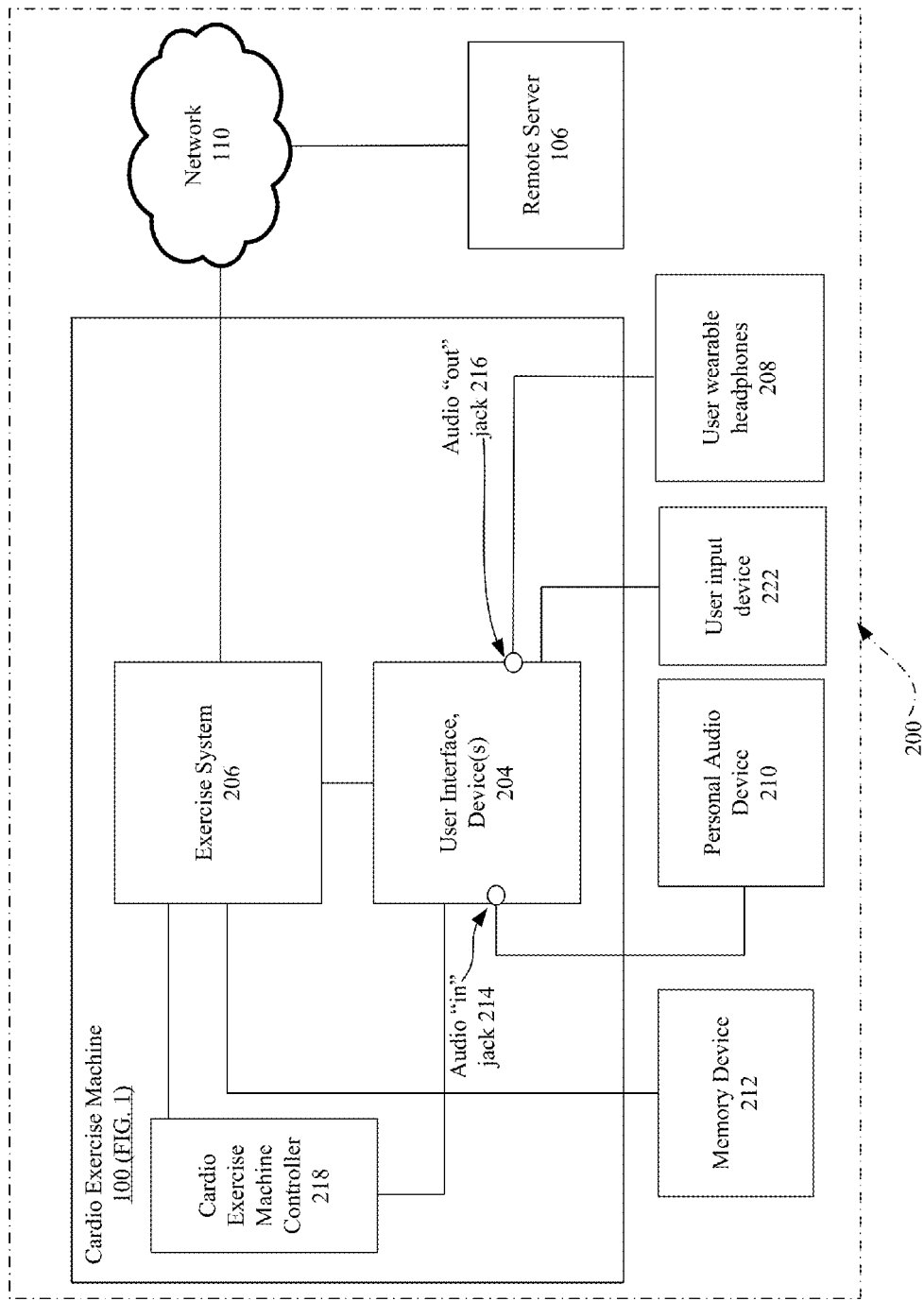
FIG. 2 is a diagram depicting an exercise apparatus that includes an exercise system.

Referring to FIG. 2, a system 200 is shown that includes a cardio exercise machine 101 such as the treadmill shown in FIG. 1. The cardio exercise machine 101 includes an exercise system 206 that controls functions relating to the operation of the cardio exercise machine, data management, and interactions with a user. The exercise system 206 can be implemented in a plurality of ways. In some examples, the exercise system 206 is implemented as a processor board and/or software. The processor board can be installed in, on, or near the cardio exercise machine 101 and may be mounted internally or externally. The software can also be configured to run on a cardio exercise machine's existing software platform that mimics the features of a customized processor board and software.

Memory device 212 communicates with the exercise system 206 in one or more of the previously-described manners to, among other things, control the operations of the cardio exercise machine 101. The mechanical operation of the cardio exercise machine 101 is controlled, for example, by a cardio exercise machine controller 218 that can receive instructions from a plurality of sources. A user controls the operations of the cardio exercise machine 101 directly via a user input device 222 (e.g., by actuating a button that manually increases the speed of a conveyer belt on a treadmill).

User input device 222 includes buttons (e.g., pressure-sensitive buttons, a touch screen, etc.), dials, a keypad, and other mechanisms that allow a user to input data into the exercise system. User interface, devices 204 includes a graphical display (e.g., an LCD screen, a series of LED lights, etc.) and/or a speaker to provide audio feedback to the user. The user interface, devices 204 communicates with the exercise system 206 to provide audio and visual feedback about the performance of the user during a workout program, and to provide operating details related to the cardio exercise machine (e.g., a display of the user interface, devices 204 displays the time remaining in the current workout program).

The exercise system 206 also provides audio feedback to the user that is coordinated with the playback of user-provided audio content provided by a personal audio device 210. The personal audio device 210 communicates with the user and the exercise system via any of the connection techniques described above. In the example of FIG. 2, the user receives audio (e.g., music, audio feedback, or guidance information) from the exercise system 206 by connecting user-wearable headphones 208 to an audio "out" jack 216. In the same example, the exercise system 206 communicates with the personal audio device 210 via audio "in" jack 214. Alternatively, the exercise system 206 can receive media over a network 110 from a remote server 106, which is provided to the user via user interface, devices 204 (e.g., a display on the user interface, devices 204 could display a video to the user), or via one or more audio connection methods.

As described above, the exercise system 206 optionally communicates with a remote server 106 to transmit and receive personal and performance data, as well as workout programs and other information. In some examples, the remote server 106 publishes the personal and performance data of a user such that the user can view workout data on a website, news feed (e.g., an RSS feed), or in an email sent to the user from the remote server 106. In this way, the user can visualize, track, organize, and manage his workout progress.

Figure 3:
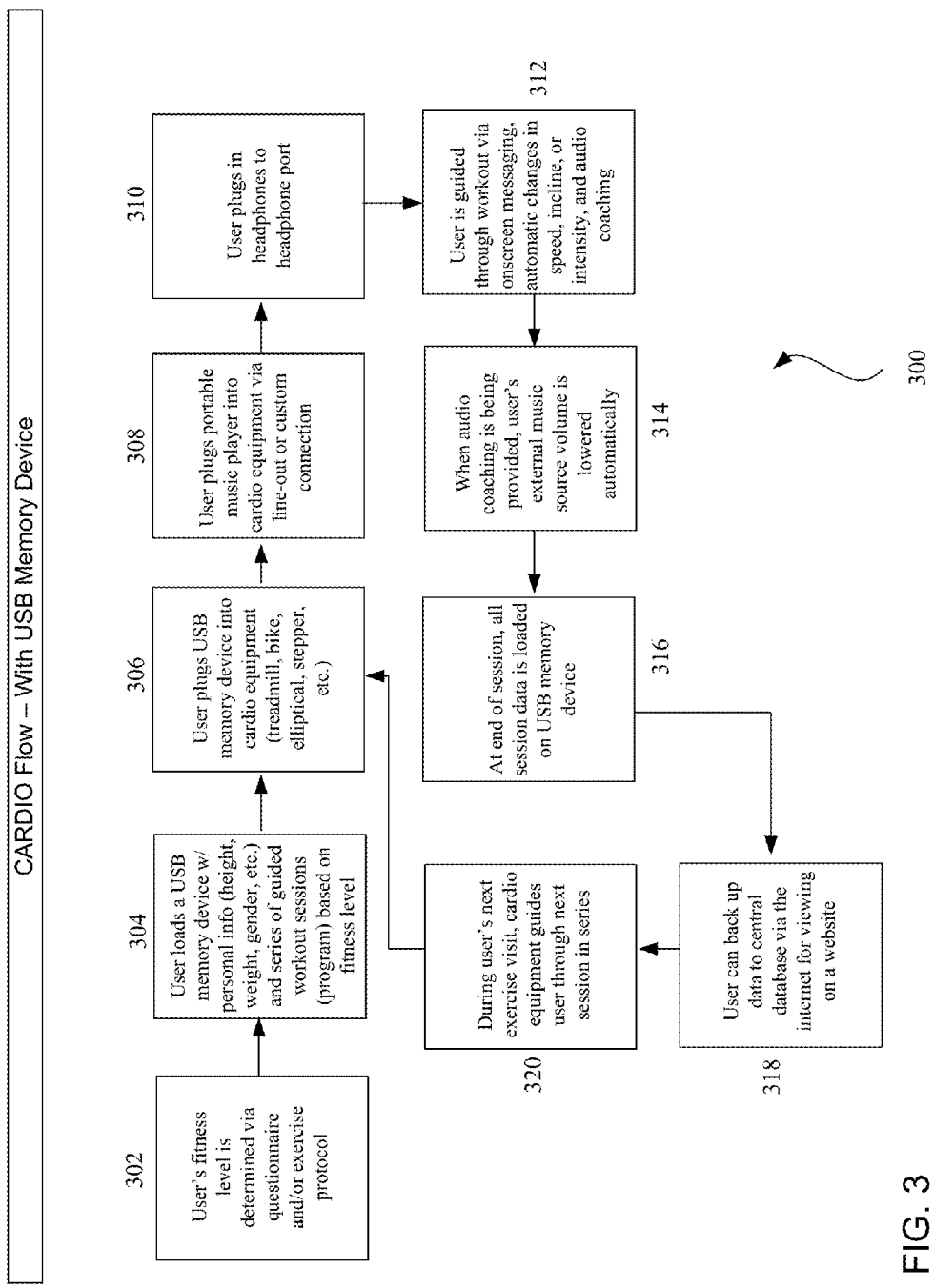
FIGS. 3 and 4 are flow charts of processing that control the exercise apparatus of FIG. 1.

Referring to FIG. 3, a process 300 to control the exercise system is shown. The process flow 300 relates to an example where a USB memory device stores user-specific data and is used in administering the workout session. If it is a user's first workout, the user's fitness level is determined 302 via the previously-described questionnaire, exercise protocol, or other method. The user loads 304 the USB memory device into the machine. The USB device includes one or more guided workout sessions that were determined by the exercise system based on the user's fitness level and are stored on the memory device. In some examples, users load new programs onto the memory device 212, via the Internet or at health club locations. The user inserts 306 the USB memory device into the cardio exercise machine, and connects 310 headphones into a provided jack. The user begins operation of the cardio exercise machine, and is guided 312 via one or more of on-screen messaging, automatic adjustments in speed, incline, or intensity, or audio coaching.

When the cardio exercise machine is attempting to provide audio coaching to the user, the cardio exercise machine lowers 314 the volume of the user-provided audio content (e.g., the music playing on the user's mp3 player). Similarly, the cardio exercise machine restores the volume of the user-provided audio content after the audio coaching has been provided. In another example, an imbedded device manages cardio exercise equipment with user-specific exercise programming and activity tracking That is, the removable storage functionality is not necessary in some implementations.

Figure 4:
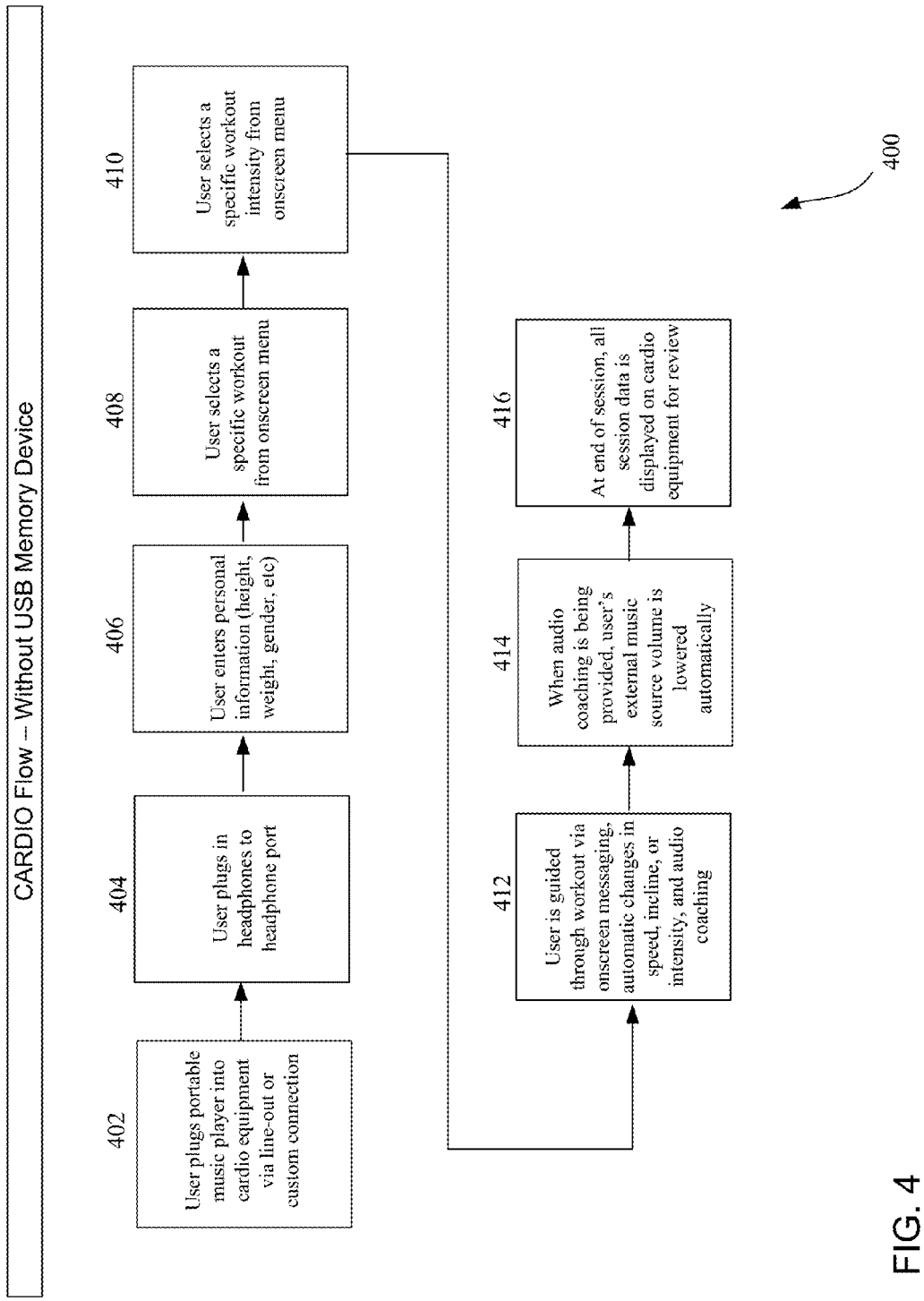

Referring to FIG. 4, a process 400 to control the exercise system is shown. The user connects 402 a personal audio device to the exercise system and also connects 404 headphones to a headphone jack (e.g., a port on the cardio exercise or machine, a port on the personal audio device, depending on the configuration). The user enters 406 personal information into the exercise system using the user interface, devices 204 (FIG. 2).

In some examples, an exercise system includes a set of "pre-loaded" exercise sessions that are selectable by the user. Cardio programs are personalized to each user's level of fitness using a number of factors, including an on-machine testing protocol, and other factors described above. The user selects 408 a workout from an onscreen menu, or from a list of workouts provided audibly to the user from the exercise system. The user can also select 410 custom options relating to the workout (e.g., the intensity of the workout, the type of workout, etc.). The exercise system provides 412 exercise guidance and instruction via a combination of on-machine messaging, automatic machine control of speed, incline, intensity, etc. via the CSAFE protocol or other proprietary protocols, and audio-based coaching and content.

Again, for the audio coaching, two levels of interaction exist. First, a user can connect an existing personal audio device (e.g. iPod, MP3 player, CD player, etc.) into a line-in jack on the processor board, connect headphones into a line out jack on the new processor board, and then the software will automatically fade 414 the user-provided audio (e.g., music) while playing the audio coaching information. The user's music will then resume playing during time intervals where coaching information is not being transmitted. A user can also connect headphones into a line-out jack on the processor board, and then the software will play the audio coaching information. The processor board can also provide music or other content when coaching information is not being transmitted.

At the end of the session the user's performance data is displayed 416 on the screen. Audio content and messaging may be fixed for the life of the machine, or could be updated via a management function or future networking of the equipment.

Figure 5:
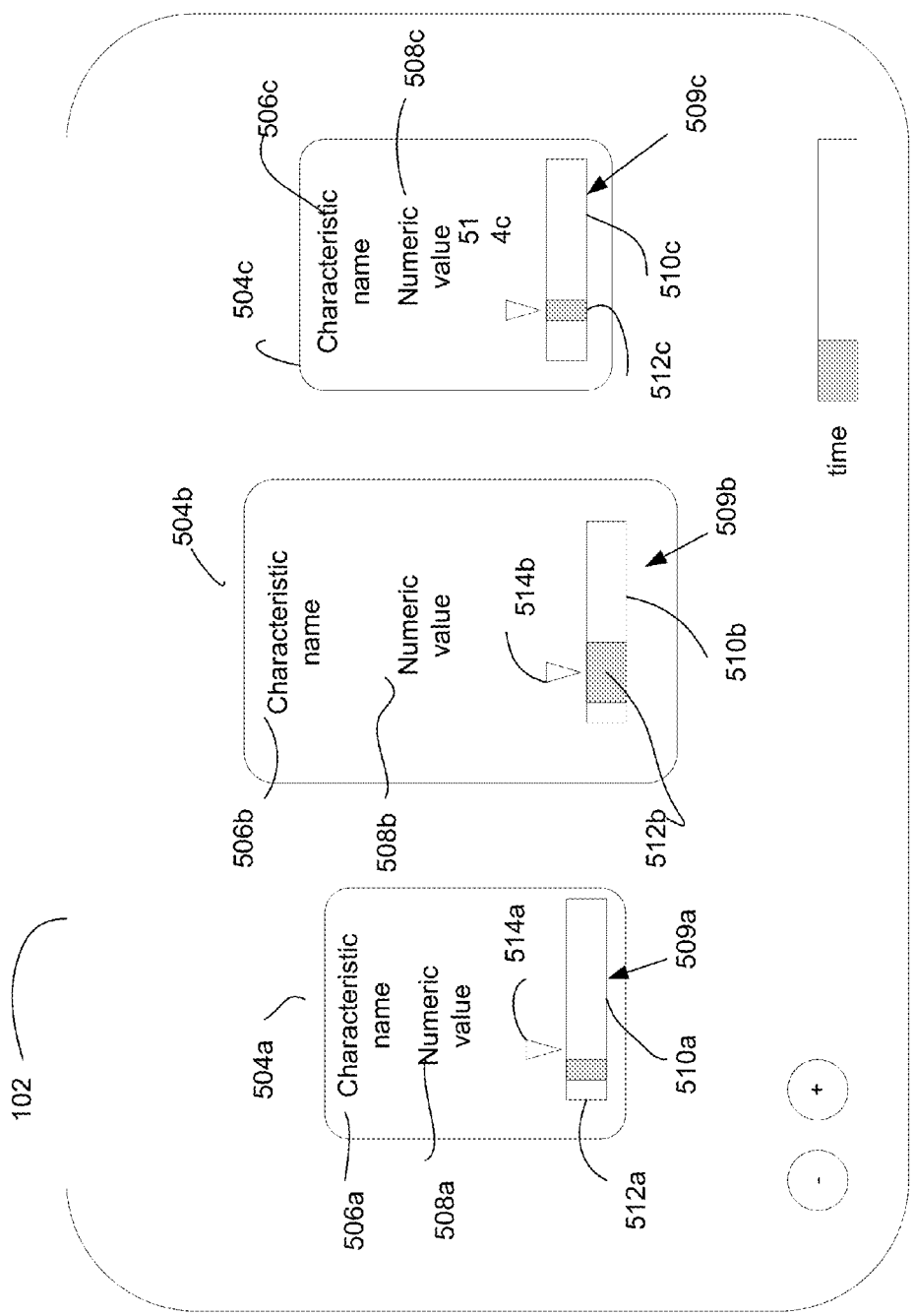
FIG. 5 is a diagram depicting details of a user performance screen.

Referring to FIG. 5, the display 102 for the cardio exercise machine (here the treadmill of FIG. 1) has the display 102 displaying various user interfaces, such as a graphical user interfaces with the questions as mentioned above for the treadmill prior to the user performing the exercise. As shown in FIG. 5, the display 102 displays user's performance during exercise. As mentioned, the system 200 calculates the user's level of fitness based on the answers to the questions, as discussed above. The system 200 also determines a standard for the user based on the type of exercise machine and the user's prior performance on that type of equipment. For example, for a treadmill one standard is calculated whereas for an elliptical machine a different standard is calculated. FIG. 5 illustrates the touch screen display 102 rendering exercise performance to the user in relation to the determined standard for a treadmill machine, as plural visual performance data items 504a-504c. The rendered exercise performance is provided by the system 200 to the touch screen display 192 and includes visual performance data items 504a-504c that include performance characteristics according to the type of machine. Thus, for the treadmill, the performance characteristics include platform incline, speed, and resistance level. On the other hand for an elliptical machine the performance characteristics would include cross ramp (ramp angle of the ramp platform for the trainer), strides per minute and resistance level performance characteristics.

In FIG. 5, each visual performance data item 504a-504c is rendered as a dynamic visualization with respect to the predetermined standard for each performance characteristic in real time. Thus for the treadmill, each visual performance data item 504a-504c includes the characteristic's name 506a-506c, a numeric value 508a-508c, and a pacer set 509a-509c comprising a range depiction 510a-510c, i.e., a min/max range, a calculated performance standard range 512a-512c that various with exercise performance within the range depiction 510a-510c, and a performance indicator 514a-514c that indicates the operator's performance with respect to that characteristic. The performance standard adopted for a particular machine will vary according to the machine, and therefore the system 200 calculates a performance standard for each performance characteristic. Also displayed is a time indicator that displays the time period of the particular exercise instruction and how much time the user has currently performed the instruction.

For other cardio machines visual performance data for other performance characteristics against calculated standards would be displayed. For example, visual performance data for an elliptical machine typically would include cross ramp angle (for machines that vary ramp angle), strides per minute, and resistance level performance characteristics. For other machines, visual performance data for, e.g., a stationary bicycle would include rotations per minute (rotational speed) and resistance level. In other examples, visual performance data can also be determined for stair-climbers, rowing machines and ski-trainers. These examples would use calculated performance standards for each performance characteristic for each type of machine and would typically include speed and resistance level performance characteristics and in some examples incline.

More specifically, the visual performance data displays each visual performance data item 504a-504c during exercise, represented by user performance pace indicators 514a-514c that are rendered within a graphically delineated regions that defines a lower limit of the characteristic and an upper limit of characteristic. Also displayed in each visual performance data item 504a-504c on the display is the system 200 determined approximate standard that is based on factors particular to the machine and the user represented by the calculated performance standard range 512a-512c. The user matches exercise performance as represented by the user performance indicators 514a-514c with angle, speed and resistance in the treadmill system, with the calculated angle, speed and resistance calculated performance standard range 512a-512c. As the operator 12 runs on the track of the cardio system sensors that monitor belt motor speed or belt speed relay the speed of the belt to the system 200. The system uses this data with the calculated standard for each of the measured performance characteristics to generate the graphical interface to render the platform angle, speed and resistance level performance characteristics visually as corresponding user indicators in relation to corresponding calculated performance. Also displayed as part of the visual performance data are calculated/determined numeric values for each of the performance characteristics.

When the user performance indicator 514a-514c is outside a calculated performance standard range 512a-512c, the user would need to adjust the user's pace to match the speed of the calculated performance standard range 512a-512c. The system 200 may further include a notice instructing the user to terminate exercising the current exercising instruction once the operator cannot maintain the user performance indicator 514a-514c within the calculated performance standard range 512a-512c.

Figure 6:
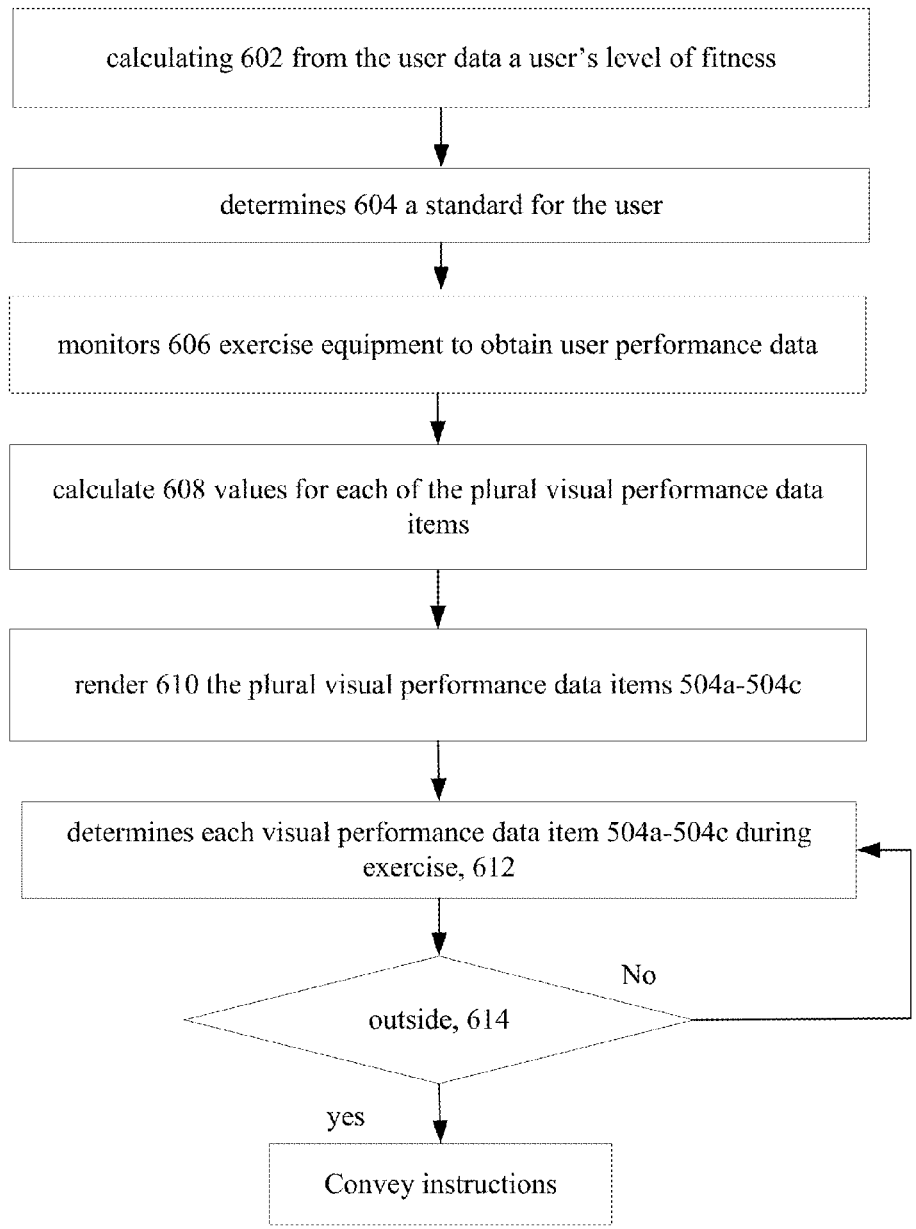
FIG. 6 is a flow chart depicting details on user performance guidance.

Referring now to FIG. 6, the system 200 produces the visual performance data items 504a-504c for the display 102 (here the treadmill of FIG. 1), by retrieving user data and calculating 602 from the user data a user's level of fitness based on the answers to the questions, as discussed above and prior user data stored on the memory device. The system 200 also determines 604 a standard for the user based on the type of exercise machine and the user's prior performance on that type of equipment. The system 200 monitors 606 exercise equipment sensors (not shown) to obtain user performance data. For a treadmill machine the system monitors the speed of the treadmill and the angle of inclination of the platform. The system calculates 608 values for each of the plural visual performance data items 504a-504c and causes 610 the plural visual performance data items 504a-504c to be rendered by the display. The touch screen display 102 renders the visual performance data items 504a-504c, by rendering each visual performance data item 504a-504c as a dynamic visualization with respect to the predetermined standard for each corresponding performance characteristic in relation to the user's performance in real time.

Thus for the treadmill, each visual performance data item 504a-504c has rendered the characteristic's name 506a-506c, the numeric value 508a-508c calculated from the monitored performance, and the calculated pacer set 509a-509c comprising the range depiction 510a-510c, i.e., a min/max range, the calculated performance standard range 512a-512c, and the determined user performance indicator 514a-514c that indicates the operator's performance with respect to that characteristic. The performance standard adopted for a particular machine will vary according to the machine, and therefore the system 200 calculates a performance standard for each performance characteristic. Also displayed is a time indicator that displays the time period of the particular exercise instruction and how much time the user has currently performed the instruction.

The system 200 determines 612 each visual performance data item 504a-504c during exercise and when the user performance indicator 514a-514c is outside 614 the calculated performance standard range 512a-512c, the system can convey audio instructions to the user to adjust the user's performance, e.g., pace on the treadmill, to match the speed of the calculated performance standard range 512a-512c or when it is critically out of scope (empirically set), render a notice instructing the user to terminate exercising the current exercising instruction once the system evaluates that the operator cannot maintain the user performance indicator 514a-514c within the calculated performance standard range 512a-512c. Various threshold can be used. For example, if the user is within a few percent, e.g., 10 percent, the system 200 can continue with the exercise, and possible can modify the exercise instruction.

On the other hand if the system 200 determines that that user is only at, .e.g., a 50% performance rate, the system 200 can tell the user to terminate the instruction. The values at which the system will cause the user to terminate could vary depending on the user and the equipment and empirical factors.

These systems may or may not be networked (wired or wirelessly) to the internet for two-way communication, session updates, program updates, device software updates, remote diagnostics, and other functions.

The various components of the system described herein may be implemented as a computer program using a general-purpose computer system. Such a computer system typically includes a main unit connected to both an output device that displays information to a user and an input device that receives input from a user. The main unit generally includes a processor connected to a memory system via an interconnection mechanism. The input device and output device also are connected to the processor and memory system via the interconnection mechanism.

One or more output devices may be connected to the computer system. Example output devices include, but are not limited to, a cathode ray tube (CRT) display, liquid crystal displays (LCD) and other video output devices, printers, communication devices such as a modem, and storage devices such as disk or tape. One or more input devices may be connected to the computer system. Example input devices include, but are not limited to, a keyboard, keypad, track ball, mouse, pen and tablet, communication device, and data input devices. The invention is not limited to the particular input or output devices used in combination with the computer system or to those described herein.

The computer system may be a general purpose computer system which is programmable using a computer programming language, a scripting language or even assembly language. The computer system may also be specially programmed, special purpose hardware. In a general-purpose computer system, the processor is typically a commercially available processor. The general-purpose computer also typically has an operating system, which controls the execution of other computer programs and provides scheduling, debugging, input/output control, accounting, compilation, storage assignment, data management and memory management, and communication control and related services.

A memory system typically includes a computer readable medium. The medium may be volatile or nonvolatile, writeable or nonwriteable, and/or rewriteable or not rewriteable. A memory system stores data typically in binary form. Such data may define an application program to be executed by the microprocessor, or information stored on the disk to be processed by the application program. The invention is not limited to a particular memory system.

A system such as described herein may be implemented in software or hardware or firmware, or a combination of the three. The various elements of the system, either individually or in combination may be implemented as one or more computer program products in which computer program instructions are stored on a computer readable medium for execution by a computer. Various steps of a process may be performed by a computer executing such computer program instructions. The computer system may be a multiprocessor computer system or may include multiple computers connected over a computer network. The components shown in the various figures may be separate modules of a computer program, or may be separate computer programs, or may include separate modules or programs, which may be operable on separate computers. The data produced by these components may be stored in a memory system or transmitted between computer systems.

Having now described exemplary embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A method comprising:
    receiving, by a computing device disposed in a cardio exercise machine, fitness data related to a fitness level of a user;
    selecting, by the computing device, a workout program with selection of the workout program being based at least in part on the fitness data received by the computing device;
    controlling by the computing device operational characteristics of the cardio exercise machine based at least in part on the workout program that includes a predetermined performance standard for operational characteristics of the cardio exercise machine;
    generating, by the computing device, real time feedback based on the user's performance on the cardio exercise machine, according to the operational characteristics and the selected workout program; and
    rendering by the computing device the feedback on a display device on the cardio exercise machine, with the rendered feedback including a plurality of visual performance data items that include speed and resistance level operational characteristics, with each visual performance data item rendered as a separate dynamic visualization with respect to the predetermined standard for each operational characteristic.

2. The method of claim 1, further comprising:
    generating the feedback by:
    generating the plurality of visual performance data items for each of plural characteristics measured by the system.

3. The method of claim 1, wherein the plurality of visual performance data items further includes platform inclination data.

4. The method of claim 3, wherein the visual performance data items are rendered with a characteristic's name, a numeric value calculated from monitored performance, and a calculated pacer set.

5. The method of claim 4, wherein the calculated pacer set includes a range depiction, a calculated performance standard range, and a determined user performance indicator that indicates the operator's performance with respect to that characteristic.

6. The method of claim 1, wherein selecting the workout program comprises combining one or more features of respective workout programs to form the workout program.

7. The method of claim 1, wherein controlling operations of the cardio exercise machine comprises controlling one or more of a speed, incline, intensity, duration, and resistance provided by the cardio exercise machine.

8. The method of claim 1, further comprising:
    generating, by the computing device, audio feedback based on at least one of the user's operation of the cardio exercise machine and the selected workout program; and wherein the cardio exercise machine provides the audio feedback to the user through a personal audio device configured to play audio content.

9. The method of claim 1, wherein the exercise machine comprises a treadmill, stationary bicycle, stair-climber, elliptical trainer, ski-trainer, or rowing machine.

10. The method of claim 1, wherein the exercise machine is a treadmill.

11. A cardio exercise apparatus comprising:
    a machine body;
    a frame attached to the machine body;
    a display device supported by the frame;
    circuitry disposed in the cardio exercise apparatus and configured to:
    receive fitness data related to a fitness level of a user;
    select a workout program with selection of the workout program being based at least in part on the received fitness data;
    control operational characteristics of the cardio exercise apparatus based at least in part on the workout program that includes a predetermined performance standard for operational characteristics of the cardio exercise apparatus;
    generate real time feedback based on the user's performance on the cardio exercise apparatus, according to the operational characteristics and the selected workout program; and
    render the feedback on the display device, with the rendered feedback including a plurality of visual performance data items that include speed and resistance level operational characteristics, with each visual performance data item rendered as a separate dynamic visualization with respect to the predetermined standard for each operational characteristic.

12. The cardio exercise apparatus of claim 11, wherein the circuitry includes a computing device, with the computing device further configured to:

generate the feedback as visual performance data items for each of plural characteristics measured by the computing device.

13. The cardio exercise apparatus of claim 12, wherein the plurality of visual performance data items further includes platform inclination data.

14. The cardio exercise apparatus of claim 13, wherein the visual performance data items are rendered with a characteristic's name, a numeric value calculated from monitored performance, and a calculated pacer set.

15. The cardio exercise apparatus of claim 14, wherein the calculated pacer set includes a range depiction, a calculated performance standard range, and a determined user performance indicator that indicates the operator's performance with respect to that characteristic.

16. The cardio exercise apparatus of claim 12, wherein the workout program is selected by the computing device, and the selection comprises combining one or more features of respective workout programs to form the workout program.

17. The cardio exercise apparatus of claim 12, wherein the computing device controls operation of the cardio exercise machine by controlling one or more of a speed, incline, intensity, duration, and resistance provided by the cardio exercise machine.

18. The cardio exercise apparatus of claim 12, wherein the computing device is further configured to:
generate audio feedback based on at least one of the user's operation of the cardio exercise machine and the selected workout program; and
wherein the cardio exercise machine provides the audio feedback to the user through a personal audio device configured to play audio content.

19. The cardio exercise apparatus of claim 1, wherein the exercise apparatus comprises one of a treadmill, stationary bicycle, stair-climber, elliptical trainer, ski-trainer, or rowing machine.

20. The cardio exercise apparatus of claim 1, wherein the exercise machine is a treadmill.

* * * * *